United States Patent [19]

Felton

[11] 4,348,286
[45] Sep. 7, 1982

[54] LARGE SAMPLE THIN LAYER CHROMATOGRAPHY

[75] Inventor: Herman R. Felton, Wilmington, Del.

[73] Assignee: Analtech, Incorporated, Newark, Del.

[21] Appl. No.: 284,515

[22] Filed: Jul. 17, 1981

[51] Int. Cl.³ .............................................. B01D 15/08
[52] U.S. Cl. .................................. 210/658; 210/198.3
[58] Field of Search .................... 210/658, 198.3, 198.2

[56] References Cited

U.S. PATENT DOCUMENTS

| | | | |
|---|---|---|---|
| 3,511,775 | 5/1970 | Collins | 210/198.3 |
| 3,585,129 | 6/1971 | Delfel | 210/198.3 |
| 3,623,841 | 11/1971 | Kraffczyk et al. | 210/658 |
| 4,065,384 | 12/1977 | Pandey et al. | 210/198.3 |
| 4,158,626 | 6/1979 | Halpaap et al. | 210/198.3 |
| 4,261,835 | 4/1981 | Creeger | 210/198.3 |
| 4,273,653 | 6/1981 | Uihlein | 210/198.3 |

OTHER PUBLICATIONS

Abbott et al., Chem. & Ind. (London) 481 (1964) and 310 (1965).
Bazan, Jr. et al., Journ. of Lipid Research 11, 42–47 (1970).

*Primary Examiner*—John Adee
*Attorney, Agent, or Firm*—Dean R. Rexford

[57] ABSTRACT

In thin layer chromatographic plates comprising adsorbent layers characterized by adsorptivity which increases from a first edge to the edge opposite, as, for example, in wedge layer plates, resolution is improved by development in the direction of increasing adsorptivity.

3 Claims, 5 Drawing Figures

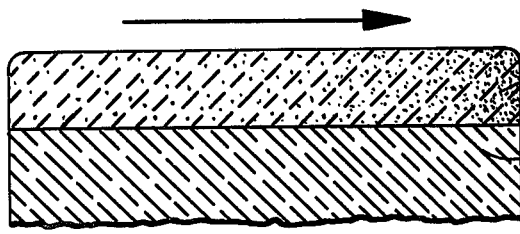
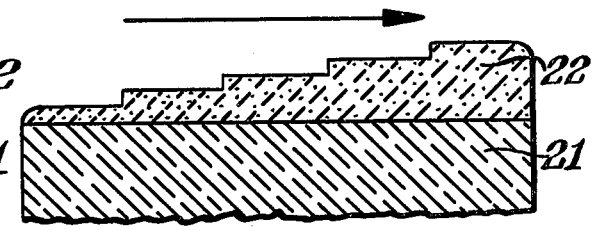
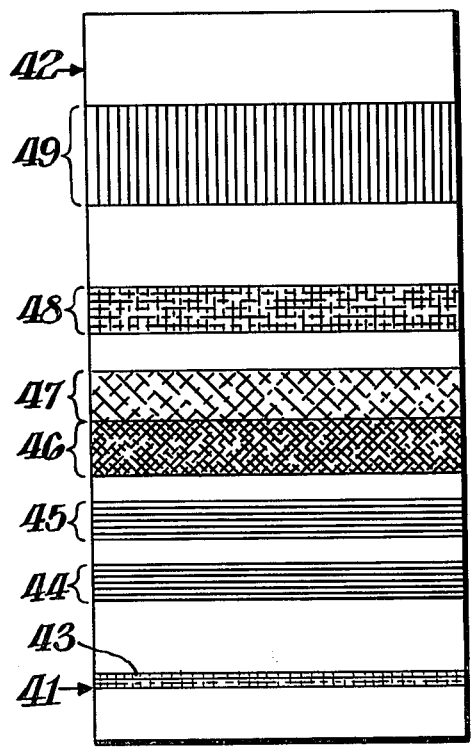
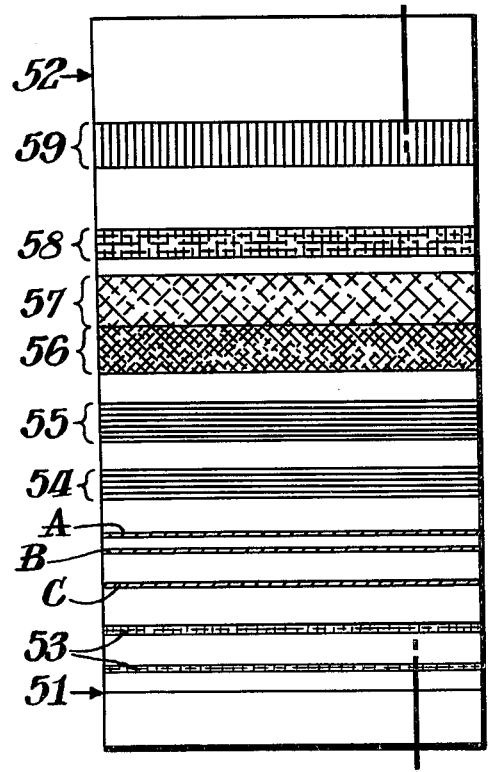
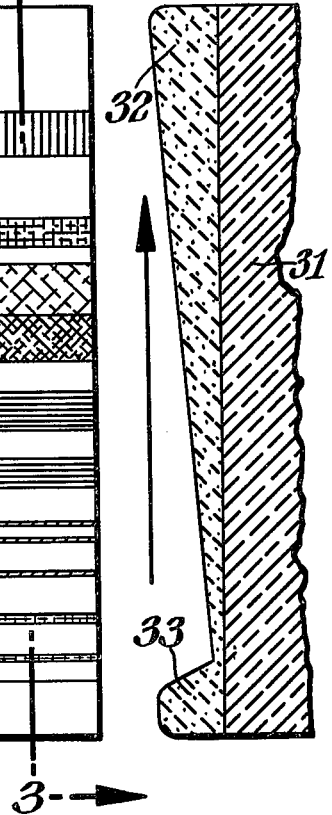

LARGE SAMPLE THIN LAYER CHROMATOGRAPHY

PRIOR ART AND BACKGROUND OF THE INVENTION

Thin layer chromatography has acquired great importance as a relatively inexpensive and easily applied analytical tool in the modern laboratory. Such chromatography employs a finely divided adsorbent, commonly silica gel or alumina, bonded in a thin, usually uniform or flat, layer on a supportive substrate, usually glass, to form a thin layer chromatographic plate, as it is called in the trade.

In use, the sample mixture to be resolved, usually one drop of solution, is placed on the adsorbent near one edge of the plate. After drying, an eluting solvent is applied to the same edge of the plate, generally by setting the plate upright in a reservoir having a small amount of eluting solvent which then rises up the plate by capillary action. The components of the sample mixture move with the eluting solvent at rates which are inversely proportional to the strength of their attraction to the adsorbent, relative to the solubility in the solvent. Thus, on development, as it is called, the components of the mixture which, for this and other reasons, move at different rates, are distributed along the solvent path. At this point, the plate is said to be developed.

The position of a separated component on the developed plate is established by means of the intrinsic color of the component, by means of color forming reagents sprayed on the dried plate, by optical means such as ultraviolet light irradiation, or by other means depending on the properties of the components being separated.

The separated components are identified according to the distances through which they have moved, expressed as a fraction of the distance through which the solvent front has moved. These fractions are the so-called $R_f$ values and are, under standard conditions, characteristic of each component.

Commonly used plates are flat, that is the thickness of the adsorbent layer is the same over the whole area of the plate. Typically, adsorbent layers for analytical purposes are 100 to 250 $\mu$m thick. Such plates, for example those using silica gel, can accept sample solutions ranging from 1 to 20 $\mu$l, the solutions containing from about 1 to about 10 $\mu$g of solute.

Occasionally there is need to treat larger samples, for example to provide purified materials for further work (so-called preparative chromatography), or to separate components present in tiny amounts from relatively large amounts of other materials. Plates having thicker adsorbent layers up to about 2,000 $\mu$m are commercially available for such purposes. However, such plates often provide unsatisfactory resolution. There appear to be at least two reasons for this. Firstly, as is obvious, large sample volumes, even on thick absorbent layers, will produce large sample spots wherein the components at the starting line are distributed over the area of the spot. It follows, of course, that a diffuse starting spot (or line as is generally used in preparative chromatography) will produce a diffuse distribution of component spots (or bands) on development and components having similar $R_f$ values will not be resolved. The other principal reason is related to the fact that in thicker adsorbent layers the components are carried forward often in tear drop shape due to so-called wall effects, the component front generally lagging behind at the adsorbent-air interface. At the adsorbent-support interface, the component front either lags behind or moves ahead, depending on the wetting characteristics of the component with respect to the support. In general, the faster a component moves the more pronounced the wall effects. Finally, the slower drying of thicker adsorbent layers after development also permits greater outward diffusion of separated components from the spot or band during the drying process.

Now available in the trade is a type of chromatographic plate comprising a so-called preconcentrating zone which overcomes to a degree problems associated with diffuse sample spots or lines at the plate starting line. The preconcentrating zone comprises a granular nonabsorbent such as inactive kieselguhr or glass powder placed adjacent to the regular adsorbent along the starting edge of the plate where sample is applied. When eluting solvent is applied to the plate, all components, being unadsorbed in the preconcentrating zone, move rapidly out of the zone with the solvent front until they meet the regular adsorbent and are slowed. The result is that all components are concentrated on a thin starting line at the bottom of the adsorbent.

Other stratigems intended to improve the resolution of thin layer chromatography, usually with respect to particular components, have been disclosed. For example, Abbott et al[1] in Chemistry and Industry (London) 481 (1964) teach the use of what they call a "wedge layer plate". In this plate, the thickness of the adsorbent layer tapers from 2,000 $\mu$m at the starting edge to 100 $\mu$m at the opposite edge. Abbott et al teach the use of the thicker adsorbent at the origin to remove coextracted chlorophylls and carotenes (polar materials), i.e., to "clean up" the mixture as the authors say, in order better to resolve large $R_f$ value chlorophenoxy acid herbicides in the thinner sections.

In Chemistry and Industry 310 (1965), Abbott et al[2] teach the use of a wedge layer plate wherein the thick section of the wedge is formed from highly active material while the remainder of the layer is of less retentive composition.

Analogously, Bazan Jr. et al in Journal of Lipid Research 11, 42 (1970) teach similar wedge layer plate resolution in the thin section of trace amounts of free fatty acids in complex lipid extracts.

The wedge layer plates of the art have in common the notion of placing the largest amount of adsorbent, or the greatest adsorptivity, near the starting edge and lesser amounts in the region of the opposite edge, where the components of particular interest are to be resolved.

SUMMARY OF THE INVENTION

It has been found that resolution of components of mixtures on a thin layer chromatographic plate, having increasing adsorptivity from a first edge to the edge opposite, is improved by developing the chromatrogram in the direction of increasing adsorptivity. Increasing adsorptivity is realized inter alia by means selected from linear or stepwise increase in adsorbent thickness and by increase in the concentration of active adsorbent in a less active medium.

BRIEF DESCRIPTION OF THE DRAWINGS

FIG. 1 is a sectional view taken through an invention thin layer chromatographic plate supported on glass, wherein adsorptivity is increased from left to right, as shown, by increasing the concentration of an active adsorbent in mixture with a less active medium in that direction.

FIG. 2 is a sectional view taken through an invention plate similar to that of FIG. 1, wherein adsorptivity is increased from left to right, as shown, by stepwise increase in the adsorbent layer thickness.

FIG. 3 is a sectional view taken at line 3—3 of the invention plate of FIG. 5, wherein adsorptivity is increased from bottom to top, as shown, by linear increase in adsorbent layer thickness. The device represented by FIG. 3 includes a preconcentration zone and is a preferred embodiment of the invention.

The thickness of the layers shown in FIGS. 1, 2, and 3 are, for clarity, much exaggerated with respect to the length.

FIG. 4 shows the resolution of a mixture of dyes on a flat plate of the art.

FIG. 5 shows the resolution of a mixture of dyes on the preferred plate of the invention as shown, in section, in FIG. 3.

DESCRIPTION OF THE PREFERRED EMBODIMENTS

It is not precisely known why the employment in the invention manner of the wedge layer plates of the art results in improved resolution, particularly with large samples. Although I do not wish to be bound by theory, I speculate that the faster moving components, that is those which have high $R_f$ values which as a consequence tend to follow the solvent front closely, are particularly slowed by the increasing adsorptivity of the layer so as to emphasize small differences in $R_f$ values among the components. The result, whatever the reason, is that mixtures are often resolved, which, on a flat plate or a wedge layer plate employed in the art manner, would not be resolved. The improved resolution is not limited, however, to components of high $R_f$ value. As will be demonstrated in an example, components of $R_f$ values at least as low as about 0.1 are resolved on an invention plate whereas the same components were not satisfactorily resolved on a comparable flat plate of the art nor would the components have been satisfactorily resolved on a wedge layer plate employed in the art manner. In the latter case, such low $R_f$ materials would be overwhelmed by the many other components absorbed in the "clean up" at the thick end of the wedge, as taught by Abbott et al[1] supra.

Embodiments comprising linear and stepwise increase in the thickness of the absorbent layer, as shown respectively in FIGS. 2 and 3, have further advantage over flat plates or wedge plates employed in the art manner, in that the flow of eluting solvent is throttled in particular embodiments by the thin layer near the starting edge, thus avoiding diffusion of separated spots or lines in the thicker portions of the layers due to rapid flow as described supra.

Employment of wedge layer plates of the art in the invention manner provides the above-described benefits. However, there is also disadvantage in doing so. Application of samples, especially large samples, to the thin end of the wedge, because of the lesser concentration of adsorbent there to take up the sample solution, causes diffusion of the sample over a larger area. Although other means could be used to concentrate the sample to a thin line, such as the so-called two-solvent system of the art, it is preferred to employ a preconcentration zone.

The preparation of wedge layer plates is well known in the art, for example from Abbott et al[1]. Multiband flat plates are known from Abbott et al[2]. Combination of the means of the references to produce invention wedge plates having a preconcentration zones is well within the skill of the art worker.

The preferred adsorbent is silica gel; somewhat less preferred is alumina. Other adsorbents known in the art are operable. By way of example, the preferred adsorbent, in the form of particles of 5–20 μm diameter, average about 10 μm, is mixed with about 12 wt. % of plaster of paris ($CaSO_4 \cdot \frac{1}{2} H_2O$), and applied, preferably to glass plates, as a water slurry according to art methods. After curing and drying the plate is ready for use. Other binders, which are outside the invention, such as organic polymers, optionally crosslinked in situ, can also be employed. Kieselguhr of about 20 μm particle size is similarly, and optionally simultaneously, applied to form a preconcentration zone. Materials such as glass powder can be employed in this utility or can be used, in combination with alumina, for example, as the less active medium in the layer of the embodiment of FIG. 1.

The layer of the latter embodiment can be prepared, for example, by applying successive stripes of adsorbent containing graded amounts of less active medium, and thereafter blending the stripes. Because of the greater difficulty in preparing such layers, this embodiment is least preferred.

FIGS. 1, 2, and 3 show cross-sections of chromatographic plates of the invention prepared as described above. In FIG. 1, part 11 represents a glass support to which is bonded adsorbent layer 12. Adsorbent layer 12 has increased adsorptivity across the plate, i.e., from the left to the right as shown which is brought about, for example, by increasing the concentration of an active adsorbent such as silica gel in a less active medium, such as glass powder. The arrow shows the direction of development, i.e., the direction of flow, in use, of the eluting solvent.

In FIG. 2, part 21 is a glass support having bonded thereto adsorbent layer 22. Adsorbent layer 22 has increased adsorptivity across the plate from left to right as shown, which is brought about by stepwise increase in the adsorbent thickness. The number of steps is not critical and may vary from two to as many as about 20 on a 20 cm plate. The steps need not be of equal size. The arrow shows the direction of development, i.e., the direction of flow, in use, of the eluting solvent.

In FIG. 3, part 31 is a glass support having bonded thereto adsorbent layer 32 and preconcentrating zone 33. Adsorbent layer 32 is characterized by increasing adsorptivity across the plate from the starting edge adjacent to the preconcentrating zone, in the direction of the opposite edge. The arrow indicates the direction of increasing adsorptivity and the direction of development according to the invention. Preferably, adsorbent layer 32 is active silica gel and preconcentrating zone 33 is relatively inactive kieselguhr, both bonded with plastic of paris. FIG. 3 represents a preferred embodiment of the invention.

The invention is further illustrated by comparative tests wherein a complex mixture of dyes and accompanying impurities were resolved on the preferred plate of the invention and, at least in part, on a flat plate of the art.

Both plates comprised glass supports and were 20 cm square. The adsorbent layer of the art plate was silica gel bonded with plaster of paris (called Silica Gel G in the trade) and was 2000 μm thick. The invention plate had the form of FIG. 3. The adsorbent layer, consisting of Silica Gel G from the same batch as that in the art plate, was 250 μm thick at the starting edge and 2000 μm thick at the opposite edge. A 2000 μm thick preconcentrating zone of kieselguhr bonded with plaster of paris was provided in approximately the shape shown in FIG. 3.

The test mixture was a combination of commercial dyes as follows:

Fat Red 7 B
Sudan Green (comprising a yellow and a blue dye)
Suden Blue
Sudan II (comprising 2 orange isomers)

A solution of the test mixture was applied as a sample line to the art plate about 1 cm from the bottom of the plate. A part of the same sample solution was applied in the same way to the preconcentrating zone of the invention plate, also about 1 cm from the bottom of the plate.

After drying, the plates were set upright in a toluene vapor—saturated chamber and developed with the same solvent in the usual manner. When the solvent front had moved 10 cm, the plates were removed and dried.

The developed plates are shown schematically in FIG. 4 (art) and FIG. 5 (invention). FIG. 3 is placed "in register" with FIG. 5 in order to show the corresponding cross sections of FIG. 5.

In FIG. 4, a brown impurity remained at starting line 41 while the solvent front moved to 42. Two yellow impurities appear, scarcely resolved, at 43. A blue impurity from the Fat Red 7 B appears at 44 and the blue dye from Sudan Green appears at 45. Scarcely resolved is a first orange isomer from Sudan II at 46 and a second isomer at 47. The yellow dye from Sudan Green is well resolved at 48 and the principal component of Fat Red 7 B appears as a broad band at 49.

In FIG. 5, second digits of the parts numbers correspond to those of FIG. 4. As will be seen, nearly all bands are better resolved in that they are more cleanly separated from other bands and/or are narrower. For example, among high $R_f$ materials, the band of Fat Red 7 B (59) is less than half as wide as is the corresponding band (48) in FIG. 4. Among smaller $R_f$ materials one notes that the impurities 43, 53 are widely and cleanly resolved on the invention plate whereas on the art plate they are scarcely resolved. Impurities marked A, B and C in FIG. 5 are not seen at all on the art plate.

What is claimed is:

1. In the process of resolving the components of a sample on a thin layer chromatogram having an absorbent layer characterized by linear increase in absorbent layer thickness from a thin end to a thicker end opposite, the improvement consisting in placing the sample on the absorbent near the thin end and developing said chromatograph in the direction of increasing absorbent layer thickness, whereby to resolve components of both low and high $R_f$ values.

2. The process of claim 1 further improved by the use of a preconcentrating zone adjacent to the thin edge of the absorbent, said preconcentrating zone being thicker and less active than the absorbent.

3. In a thin layer chromatographic plate comprising a wedge layer absorbent having a thick end and a thin end, the improvement consisting in a preconcentrating zone adjacent to the thin end of the wedge layer absorbent, said preconcentrating zone being thicker and less active than the absorbent.

* * * * *